United States Patent [19]
Koch et al.

[11] Patent Number: 5,847,382
[45] Date of Patent: Dec. 8, 1998

[54] BONE DETECTOR

[75] Inventors: Jay Koch, 177 Ocean Shore Dr., Key Largo, Fla. 33037; Amos G. Fowler, Atkins, Ark.

[73] Assignee: Jay Koch, Key Largo, Fla.

[21] Appl. No.: 731,882

[22] Filed: Oct. 22, 1996

[51] Int. Cl.$^6$ ................................................. G01N 21/00
[52] U.S. Cl. .................. 250/223; 209/588; 209/938; 209/939; 100/145; 198/626.6
[58] Field of Search .................... 209/552, 555, 209/556, 559, 563, 564, 576, 577, 588, 938, 939; 198/502.1, 502.2, 626.6, 846; 100/117, 145, 121, 211; 250/221, 222.1, 223

[56] References Cited

U.S. PATENT DOCUMENTS

| | | | |
|---|---|---|---|
| 3,736,583 | 5/1973 | Smith et al. | 340/240 |
| 3,777,886 | 12/1973 | Smith et al. | 209/109 |
| 3,995,164 | 11/1976 | Ramsay et al. | 250/510 |
| 4,316,411 | 2/1982 | Keaton | 100/154 X |
| 5,026,983 | 6/1991 | Meyn | 250/223 R |
| 5,205,777 | 4/1993 | Hohenester | 100/171 X |
| 5,215,772 | 6/1993 | Roth | 209/577 X |
| 5,256,102 | 10/1993 | Heiland et al. | 452/149 |
| 5,428,657 | 6/1995 | Papanicolopoulos et al. | 378/86 |
| 5,490,218 | 2/1996 | Krug et al. | 382/100 |
| 5,681,254 | 10/1997 | Dufour et al. | 198/626.6 X |

*Primary Examiner*—Tuan N. Nguyen
*Attorney, Agent, or Firm*—Ray F. Cox, Jr.

[57] ABSTRACT

A device for detecting bone fragments in deboned poultry carried on a conveyor belt of flexible clear plastic material. Fluorescent lights are positioned under the conveyor. A second conveyor positioned above the first conveyor is made up of a linked series of rigid clear plastic slats which bear down on the deboned poultry passing over the light table in order to reduce the thickness to allow the light to show through and reveal bone fragments. A video camera positioned inside the conveyor and looking down on the flattened poultry parts is used to identify bone fragments. In another embodiment, the inspection may done by operators. In either embodiment filters, desirably rose colored, are used to enhance the visibility of the bone fragments. Computer image recognition may additionally be used to identify and reject parts with bone fragments.

18 Claims, 3 Drawing Sheets

BONE DETECTOR

BACKGROUND OF THE INVENTION

The present invention relates to the detection of bone fragments and the like in deboned meat products, and in particular, poultry. The present invention also relates to devices for the detection of bone fragments and the like using transmitted light to reveal the unwanted bone fragments.

The commercial processing of meat includes the deboning of meat. Mechanical or manual deboning of meat can efficiently debone meat with minimal wastage. These processes however, whether mechanical or manual, can leave fragments of bone in the deboned meat. This is undesirable for human consumption and can result in the rejection of meat having an excessively high proportion of meat contaminated with bone fragments. There is a tradeoff in the efficiency with which the meat is deboned (minimal meat wastage) versus high proportions of bone fragments (high rejection of bone contaminated meat). One way to overcome this tradeoff is to inspect the deboned meat to reject and rework individual portions of meat rather than rejecting entire lots. In order to be successful, the detection of bone fragments must be highly reliable and the cost must be minimized. There is thus a need for an economical but efficient means to detect bone fragments in meat, and in particular, poultry.

A number of different types of apparatus for detecting bone fragments in chicken or other meat have been patented. For example, U.S. Pat. No. 3,736,583 and U.S. Pat. No. 3,777,886 mechanically detecting the presence of bone fragments. U.S. Pat. No. 5,490,218 is a computer method using x-rays that can be applied to the detection of bone fragments in meat.

U.S. Pat. No. 5,428,657 is also a device using x-rays, while U.S. Pat. No. 5,026,983 assigned to Meyn is for a method using laser irradiation. Finally, U.S. Pat. No. 3,995,164 also uses x-rays.

U.S. Pat. No. 5,256,102 mentions optical detection of the location of bone fragments in meat. In column 3, lines 45–52, a mechanical optical detector manufactured by Sortex North America of Sacramento, Calif., is described. Also mentioned are such devices as mechanical bone detectors, sonar scanners and textural detectors.

None of these patents disclose the use of a light table or the use of an upper and lower conveyor to flatten out the meat for easier detection of bone fragments.

Mechanical detectors tend to damage the meat product, while computers, lasers, x-ray and sonar equipment and the like are complex and expensive.

SUMMARY OF THE INVENTION

These and other disadvantages and limitations of the prior art are overcome by the present invention.

The purpose of the present invention is to inspect boned poultry parts for hidden bone fragments. The device comprises a first conveyor with a belt of flexible clear plastic material. A number of fluorescent lights, sealed against moisture, are positioned under the conveyor. A second conveyor is positioned above the first conveyor. The second conveyor is made up of a linked series of rigid clear plastic slats which bear down on the deboned chicken parts passing over the light table. This is necessary since thicker parts are too thick for the light to show through and reveal the bone fragments. The lower conveyor is support by a skid plate which produces a wider opening for the parts to enter the narrower gap between the two conveyors so that parts of any thickness can be accommodated and flattened to the same thickness while passing over the light table. The skid plate is manually adjusted vertically and the angle of entry can be varied. The parts generally regain their normal thickness after passing through the conveyor. Chains and pulleys synchronize the motion of the upper and lower conveyors.

The upper conveyor is configured so that it is rectangular in side outline. The inspection operator looks down on the flattened product searching for defects. A video camera or other optical means can also be positioned inside and looking down on the flattened parts. In another embodiment, the inspection may done by operators wearing rose colored glasses. The rose color gives good contrast to the bone fragments. Other filters may be used for maximum contrast. With the video camera, the operator need not be in immediate proximity to the machine which has safety advantages.

The video camera also has the advantage that it allows for the addition of computer image recognition if such is economically justifiable. A computer is able to take the video image and enhance it to reveal the bone fragments. The video camera may also use a rose colored filter. A final advantage of the use of a computer is that the computer may be used to automatically reject parts with identified bone fragments.

It is therefore an object of the present invention to provide for a bone detection apparatus to detect bone fragments in deboned meat, and in particular poultry.

It is also a object of the present invention to provide for a bone detection apparatus which is efficient in detecting bone fragments and economical to construct and operate.

It is a further object of the present invention to provide for a bone detection apparatus which does not excessively damage the deboned meat parts.

It is an additional object of the present invention to provide for a bone detection apparatus which may be operated manually or may be automated with computer detection and rejection of bone fragment containing meat products.

These and other objects and advantages of the present invention will be apparent from a consideration of the detailed description of the preferred embodiments in conjunction with the drawings which are briefly described as follows:

DETAILED DESCRIPTION OF THE PREFERRED EMBODIMENTS

Figure 1:
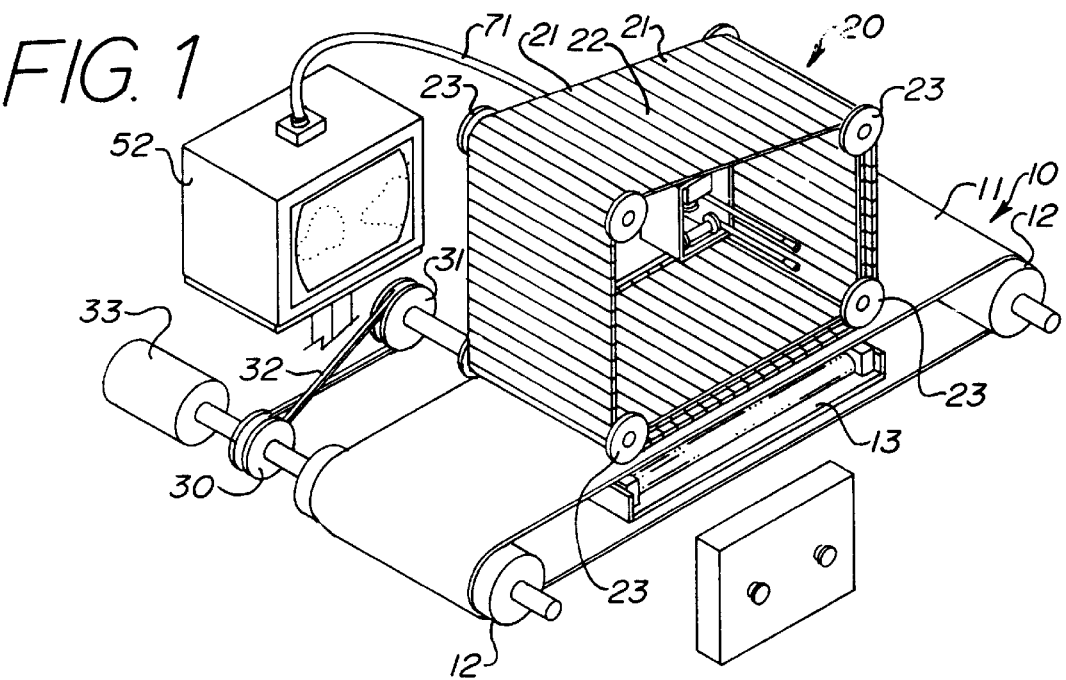
FIG. 1 is a perspective view of the bone detection apparatus of the present invention.

The present invention may be generally described with reference to FIG. 1.

The bone detection apparatus of the present invention consists of a transparent belt conveyor, designated generally as 10. A clear flexible belt 11 is operated between a pair of rollers 12. Nylon has been found to have acceptable light transmission characteristics and durability, although the present invention is not limited thereto. A rigid transparent skid plate 14 is provided under the top part of the flexible belt 11. The skid plate 14 can be adjusted to accomodate different thicknesses of product by any of various means well known in the art. The angle of the plate 14 is also adjustable to adjust the entry gap for the product. The skid plate 14 is desirably constructed so that a wider gap is formed at the entry point for the poultry product 40 so that its original thickness can be accomodated and received into the gap and gradually reduced in thickness as it proceeds between the flexible belt 11 and the upper belt 22 as described following.

A light source 13 is mounted below the belt 11. It has been found that a plurality of approximately 9 1½ inch fluorescent light tubes works well in the application of the present invention.

A second conveyor, generally designated as 20, is mounted over the transparent belt conveyor 10. The second conveyor is comprised of individual rectangular slats 21 of rigid transparent material, desirably acrylic. The slats 21 are linked together to form an endless upper belt 22. Drive chains may be provided along the edges of the slats 21. The upper belt 22 is driven around four rollers 23 which are arranged in a rectangular configuration so that the base portion 24 of the rectangle is deployed in close proximity above the flexible belt 11. The sides 25 of the rectangle define an open space above the base portion 24, as will be described more fully hereinafter.

The belt conveyor 10 and the upper second conveyor 20 are mechanically interconnected by pulleys 30, 31 and drive chain 32 to run in the same direction at similar speeds. Both conveyors 10, 20 are powered from motor 33.

Figure 2:
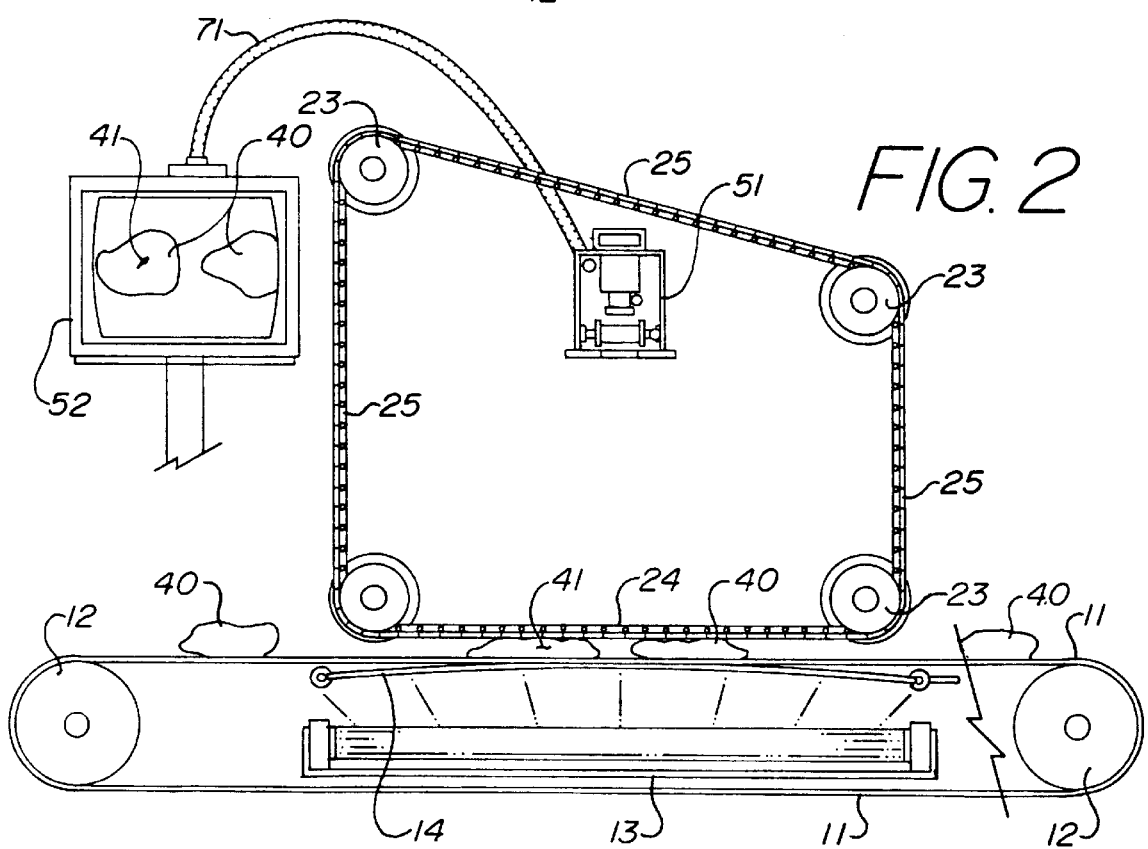
FIG. 2 is a left side elevation of the bone detection apparatus showing an embodiment in which a video camera is used to view the bone fragments.
Figure 2A:
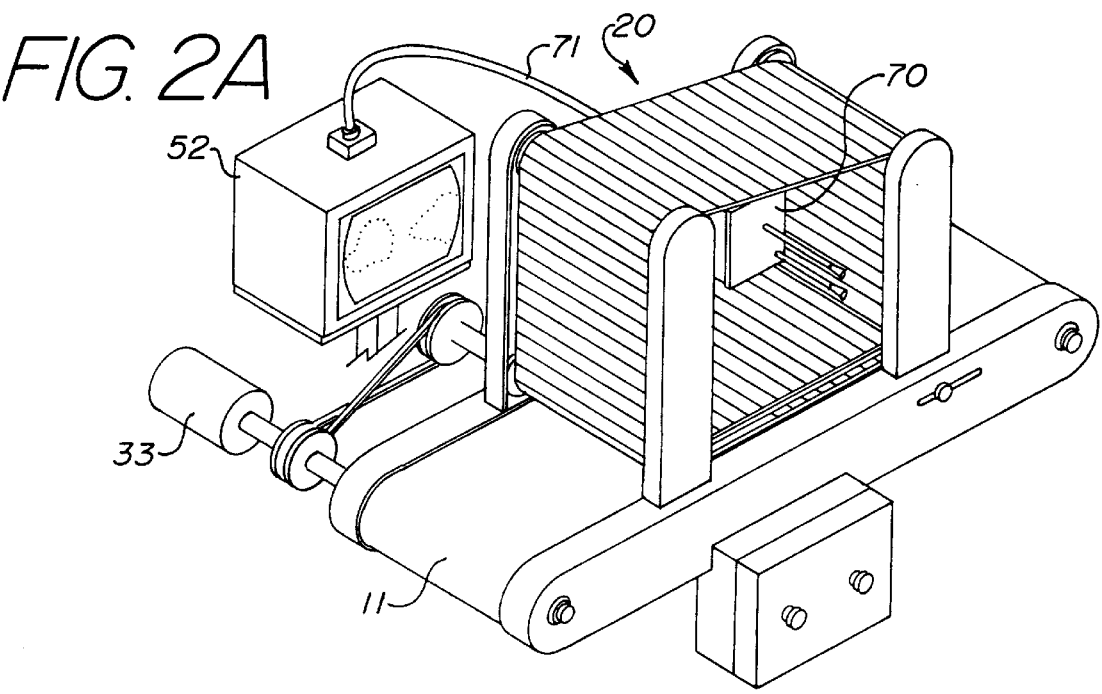

The operation of the present invention may be described with reference to FIGS. 1 and 2. The meat/poultry products 40 are placed on the flexible conveyor belt 11. The belt 11 moves the product 40 forward, passing the product 40 under base portion 24 of the rigid second conveyor 20, thereby compressing the meat product 40 to a desired thickness. The thickness of the meat product 40 may be adjusted by adjusting the separation distance between the base portion 24 of the second conveyor 20 and the skid plate 14 under the upper portion of the flexible belt 11. Excessive compression of the meat product is undesirable as this contributes to fluid loss which reduces the value of the product. It is desirable therefore to adjust the separation distance to no more than the minimum required to obtain adequate transmission of light through the meat product 40.

The light source 13 pumps light through the transparent flexible belt 11 illuminating the flattened meat product 40. The slats 21 pressing against the product 40 form a flat window against the meat product 40 to enhance vision in all parts of the product 40. Bone fragments 41 and other defects which are unable to pass light as well as the meat itself are seen in contrast to the color of the meat product.

Figure 5:
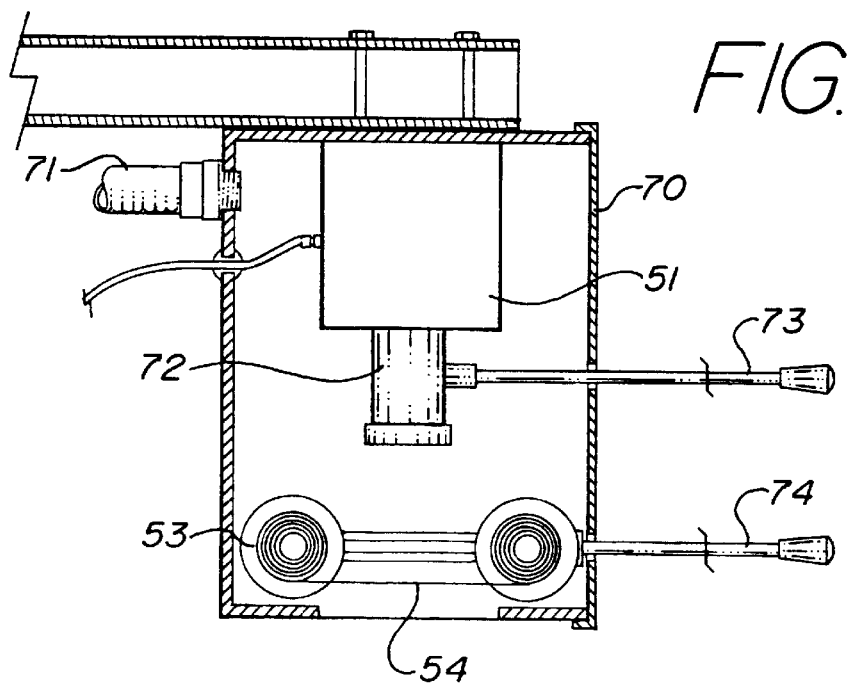
FIG. 5 is a left side elevation of an alternative embodiment of the video camera of FIG. 1 showing a filter changing mechanism.

As described above, the second conveyor 20 is designed to allow sufficient inside clearance so that an operator 50 can look at an angle down on the product 40 to determine the presence of defects 41, such as bone defects, foreign matter, blood spots, etc. In one embodiment therefore, the space within the second conveyor contains a small analog or digital video camera 51 which allows the image to be observed on a video monitor 52 or computer system. As shown in FIG. 5, the video camera 51 may contain a reel to reel filter system 53 which allows the operator or computer to adjust the filter medium 54 to use various color and contrast enhancement filters while observing the product 40. In the preferred up to 24 filter colors have been found to be desirable. The video camera 51 and filter system 53 may conveniently placed in a housing 70. The housing 70 is connected by hose 71 to the video monitor 52 for connection to a suitable supply of air to the housing 70 to prevent foggin and condensation. The video camera 51 may be provided with an adjustable iris 72 which may be adjusted under computer control or by means of a manual external iris adjustment 73 which allows control of light entry into the video camera 51 to maximize contrast between defects 41 and the meat product 40.

In addition, manual external filter control 74 may be used to select the filter which maximizes contrast. For example, it has been determined that a rose colored filter is exceptionally effective in improving the visibility of bone fragments and other defects in poultry breasts. If the detection is being done directly by the operator 50, the operator may wear rose colored glasses to the same purpose.

Figure 3:
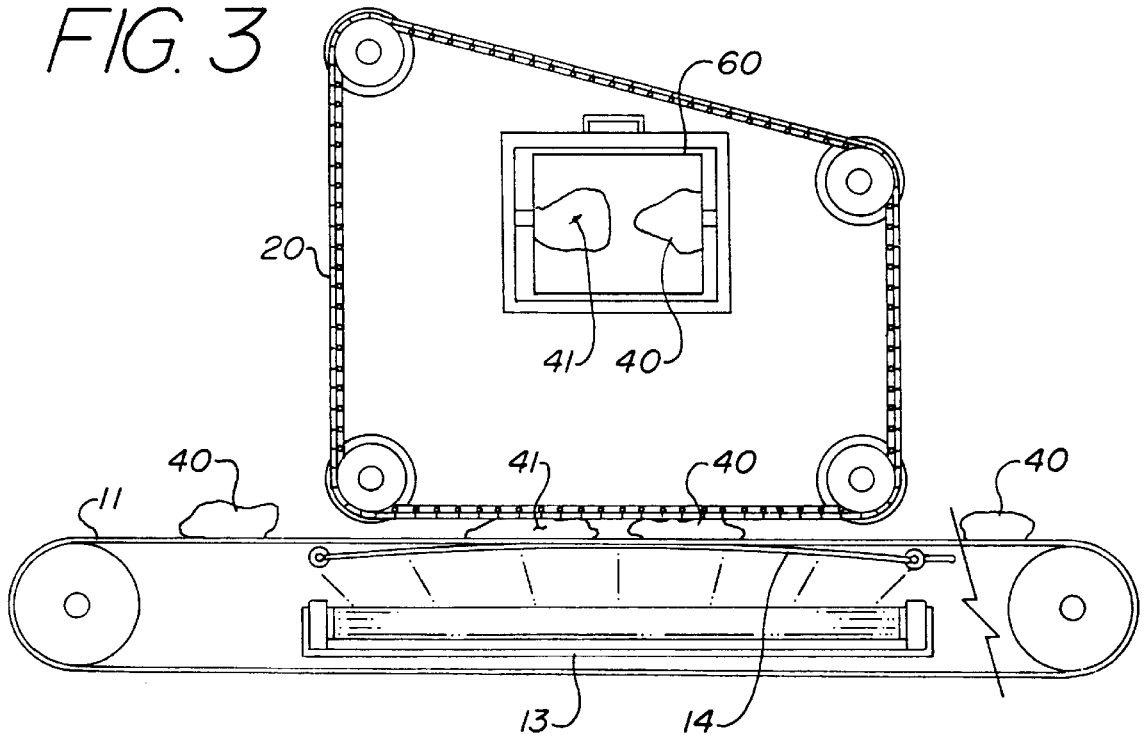
FIG. 3 is a left side elevation of the bone detection apparatus showing an alternative embodiment in which an optical apparatus, either a mirror or prism, is used by an operator to view the bone fragments.
Figure 4:
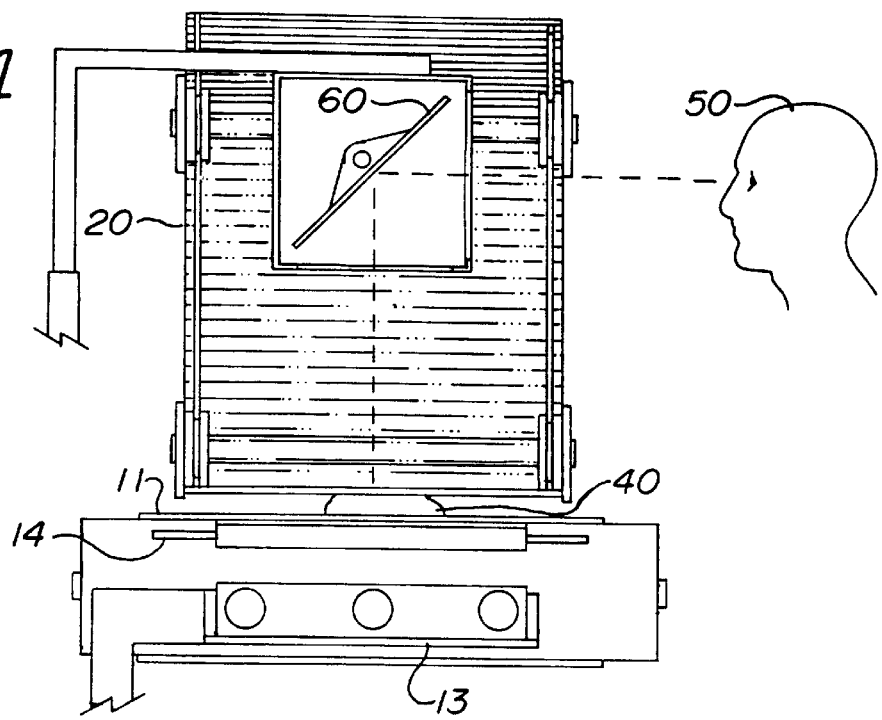
FIG. 4 is a sectional front elevation view of the embodiment of FIG. 3.

As an alternative to the use of a video camera 51, the detection of bone fragments 41 may be safely done by employing optical means to project an image from the flattened meat products 40 to the view of the operator 50 as shown in FIGS. 3 and 4. One example of such an optical means is a diagonal mirror or prism 60 which optically projects an image of the meat product 40 to the operator 50. As noted above, it might be desirable for the operator 50 to wear filter glasses to enhance the visibility of the bone fragments 41 or other defects.

A further embodiment of the present invention employs the video camera 51 in conjunction with a computer and image recognition software. Such image recognition software is commercially available and may be used to recognize bone fragments and automatically reject defective mean products 40, thus minimizing human labor.

Since the flattening of meat products may produce expressed moisture and fragments of flesh, the apparatus may require the addition of a washing mechanism to wash the belts free of such debris. Desirably such a wash mechanism may include air drying.

The present invention has been described with reference to certain preferred and alternative embodiments which are intended to be exemplary only and not limiting to the full scope of the inventions as set forth in the appended claims.

What is claimed is:

1. An apparatus for detecting bone fragments and other defects in deboned meat products, comprising:

a first conveyor having a belt of transparent material;

a second conveyor having a belt of transparent material;

means spacing said first and second conveyors in proximity so as to receive and flatten the deboned meat products therebetween;

a light source illuminating the deboned meat products whereby transmitted light through the flattened deboned meat products reveals the bone fragments and other defects;

light imaging means for receiving said transmitted light and projecting an image of the flattened deboned meat products revealing the bone fragments and other defects; and means for motion of said first conveyor and said second conveyor at a similar speed.

2. The apparatus of claim 1 wherein said first conveyor comprises a belt of flexible transparent plastic material.

3. The apparatus of claim 2 wherein said second conveyor comprises a belt of linked rigid transparent slats.

4. The apparatus of claim 3 wherein said means spacing said first and second conveyors in proximity comprises a transparent plate supporting said first conveyor belt and having means for adjusting the position of said transparent plate relative to said second conveyor belt whereby said deboned meat product is received and flattened between said first conveyor belt and said second conveyor belt.

5. The apparatus of claim 4 wherein said second conveyor is configured to define an internal space for receiving said light imaging means.

6. The apparatus of claim 5 wherein said light imaging means comprises a video camera.

7. The apparatus of claim 6 wherein said video camera is operationally connected to a video monitor for displaying said image to an operator.

8. The apparatus of claim 6 wherein said video camera is operationally connected to computer processing means.

9. The apparatus of claim 6 wherein said computer processing means further comprises image recognition means for detecting bone fragments and other defects from said image.

10. The apparatus of claim 5 wherein said light imaging means comprises a prism.

11. The apparatus of claim 5 wherein said light imaging means comprises a diagonal mirror.

12. The apparatus of claim 2 wherein said light imaging means further comprises light filtering means.

13. The apparatus of claim 12 wherein said light filtering means comprises a rose colored filter.

14. The apparatus of claim 6 wherein said video camera further comprises light filtering means.

15. The apparatus of claim 14 wherein said light filtering means comprises a reel to reel filter system having means to adjust color and contrast to enhance the detection of the bone fragments and other defects.

16. The apparatus of claim 15 wherein said video camera is operationally connected to a video monitor for displaying said image to an operator.

17. The apparatus of claim 15 wherein said video camera is operationally connected to computer processing means.

18. The apparatus of claim 15 wherein said computer processing means further comprises image recognition means for detecting bone fragments and other defects from said image.

\* \* \* \* \*